United States Patent [19]
Kinnunen et al.

[11] Patent Number: 6,074,667
[45] Date of Patent: Jun. 13, 2000

[54] LIPOSOMAL TRANSFECTION METHOD

[76] Inventors: Paavo Kinnunen, Punarinnantie 4, Finn-02660 Espoo; Tommi Paukku, Petkeltie 6 A 15, Finn-20540 Turku; Satu Lauraeus, Saastopankinranta 10 C 24, Fin-00530 Helsinki; Ilpo Huhtaniemi, Kotimaenkatu 12, Fin-20540 Turku, all of Finland

[21] Appl. No.: 09/083,013

[22] Filed: May 21, 1998

Related U.S. Application Data

[63] Continuation-in-part of application No. PCT/FI96/00629, Nov. 20, 1996.

[51] Int. Cl.[7] ................................. A61K 9/127
[52] U.S. Cl. ................ 424/450; 435/440; 435/252.3; 435/254.11; 560/224; 554/226
[58] Field of Search ................ 435/440, 252.3, 435/254.11, 257.2; 560/224, 155, 252; 554/226, 227, 223

[56] References Cited

FOREIGN PATENT DOCUMENTS

WO 93/03709 3/1993 WIPO .
WO 95/03039 2/1995 WIPO .

OTHER PUBLICATIONS

Singhal et al. Gene Transfer in Mammalian Cells Using Liposomes as Carriers. Gene Therapeutics. Ed. Jon A. Wolff, Mar. 1994.

Koiv et al. Binding of DNA to Liposomes Containing Different Derivatives of Sphingosine. Chem. Phys. Lipids. 72: 77–86, Feb. 1994.

Orkin et al. Report and Recommendations of the Panel to Assess the NIH Investment in Research on Gene Therapy, Dec. 1995.

*Primary Examiner*—David Guzo
*Assistant Examiner*—Jon Shuman

[57] ABSTRACT

An improvement in a method for transfecting a cell with a nucleic acid the improvement comprising contacting the cell with a liposomal transfection composition comprising the nucleic acid, sphingosine or a derivative thereof, having a protonable amino group in the sphingosine moiety, and at least one helper lipid.

32 Claims, 6 Drawing Sheets

LIPOSOMAL TRANSFECTION METHOD

CROSS REFERENCE TO RELATED APPLICATIONS

This application is a continuation-in-part of International Application No. PCT/FI 96/00629, filed Nov. 20, 1996 and designating the United States, entitled LIPOSOMAL TRANSFECTION METHOD, which prior application is incorporated herein by reference.

FIELD OF INVENTION

The present invention relates to a method of transfecting a cell with nucleic acid, such as DNA, using, as the transfection vector, a liposomal composition comprising a sphingosine derivative having a protonated amino group in the sphingosine moiety. The protonated amino group provides for the required cationic nature of the liposome for forming a complex with the negatively charged nucleic acid. According to the invention it was shown that the sphingosine containing liposomal composition, which had been pre-incubated with nucleic acid, such as DNA, transfected efficiently the cell lines tested.

BACKGROUND OF THE INVENTION

Liposomes are widely used for drug delivery and for delivery of foreign DNA to mammalian cells, and they offer several advantages in this respect. Such advantages are ease of manufacture, commercial availability, the possibility of targeting to specific cells or tissues, and high transfection efficiency. Cationic liposomes, that is liposomes comprising at least some positively charged lipids to give an overall positive charge to the liposomes, have been used for gene transfer, i.e. transfection of DNA, into mammalian cells both in vivo and in vitro. Due to charge interactions, the positively charged liposome forms easily, in a simple mixing process, on its surface a complex with the negatively charged DNA. The complex in turn binds strongly to the cell surface due to favorable charge interactions followed by internalization of the complex into the cell and expression of the gene (Singhal, A. and Huang, L. (1994) *Gene Thera-Pautics* (ed.: Wolff, J. A.) pp 118–142, Birkhauser, Boston).

Various cationic lipids have been suggested in the art for incorporation into liposomes, including quaternary ammonium detergents, e.g, cetyltrimethylammonium bromide (CTAB), cationic derivatives of cholesterol and diacyl glycerol, e.g. 1,2-dioleyl-3-(4'-trimethylammonio) butanoyl-sn-glycerol (DOTB), and lipopolyamines, e.g. lipopoly-L-lysine (LPLL). Also commercial preparations are available. Lipofectin® "LIPOFECTIN" is a widely used commercial preparation comprising N-[1-(2,3-dioleyloxy) propyl]-N,N,N-trimethylammonium chloride (DOTMA) in combination with dioleoylphosphatidylethanolamine (DOPE) (Gibco). The apparent toxicity of some of the commercially available products have been referred to the non-natural, non-biodegradable nature of compounds contained by them (Singhal et al, ibid).

The cationic liposomes used as a transfection vector commonly contain, in addition to the cationic lipid, a neutral or negatively charged lipid, so called helper lipid or co-lipid, the above mentioned DOPE being one such neutral helper lipid. Also other helper lipids have been suggested. Such helper lipids are typically phospholipids, and besides DOPE, e.g. dioleoylphosphatidylcholine (DOPC), dioleoylphatidylserine (DOPS), the corresponding dilauroyl, dimyristoyl and dipalmitoyl compounds, phosphatidic acid, phosphatidylglycerol, sterols, such as cholesterol, and mixtures of these have been suggested. The mono-, di- and triglycerides may be mentioned as further neutral helper lipids. A main function of the helper lipid is to fuse into and stabilize the liposome bilayer structure. It is also known that DOPE, in addition to the liposomal stabilizing effect, aids in the cytoplasmic delivery of DNA in the cell.

A wide variety of patent literature is available disclosing various cationic lipids for use for transfection, see e.g. U.S. Pat. No. 5,264,618, WO 93/03709, and WO 95/17373, just to mention a few.

Although a number of advantages are obtained by using cationic liposomes as carriers for DNA, rather than neutral or anionic liposomes, many problems still remain both in in vivo and in vitro applications. A major problem with many of the cationic lipids is that they are generally toxic to the cells, and thus of limited use. This is especially true of "LIPOFECTIN", the DOTMA component of which is a diether, and not-readily degraded in vivo and toxic to tissue cells. Thus DOTMA is not optimal from the point of view of in vivo gene delivery.

According to the invention it has now been discovered that by using a specific group of cationic lipids for inclusion into the transfection vector, it is possible to provide a method of transfection displaying clearly improved transfection efficiencies with minimal toxicity problems to the transfected cells.

SUMMARY OF THE INVENTION

The object of the present invention is thus a method for transfecting a cell with a nucleic acid which comprises contacting the cell with a liposomal transfection composition comprising a nucleic acid, sphingosine or a derivative thereof, having a protonated amino group in the sphingosine moiety, and a helper lipid.

DETAILED DESCRIPTION OF THE INVENTION

Sphingosine derivatives are amphiphilic lipids, i.e. they comprise an amino alcohol substituted with a single fatty chain. Several sphingosine derivatives occur naturally in mammalian and non-mammalian cells, and they can be degraded in connection with normal cellular metabolism. The role of sphingosines in influencing DNA synthesis and gene expression is however, largely unknown. It is also known that sphingosine and some of its cationic derivatives in liposomal form bind strongly to DNA (Koiv, A. and Kinnunen, P. K. J., *Chem. Phys. Lipids*, 72 (1994) 77–86. Another feature of the sphingosine is its ability to inhibit the protein kinase C (PKC). The inhibition of PKC has been proposed to be a critical factor determining the transfection efficiency and toxicity of a given liposome vector (Singhal et 21., ibid. p. 125). Sphingosine containing liposomes have not been suggested for use in transfection vectors, apparently due to the fact that sphingosine, being a PKC inhibitor, would be expected to resist transfection. According to the invention it has now, however, been discovered that this is not the case, and that substantially enhanced transfection efficiencies, without appended toxicity to the cells, can be obtained, as compared to using Lipofectin® "LIPOFECTIN", by including, in the liposome vector, at least one positively charged sphingosine derivative.

The main criteria when choosing the sphingosine derivative to be used according to the invention is that the amino group in the sphingosine moiety is in protonable form, in order to provide for the necessary overall cationic nature to the liposome vector formed by the sphingosine compound and the helper lipid. The cationic nature of the liposome in turn is critical for the efficient binding of the negatively charged nucleic acid to the surface of the liposome. Especially contemplated for use in the invention are the sphingosine derivatives having the following general formula

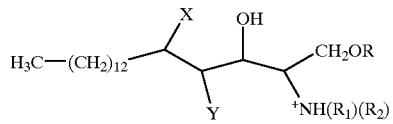

wherein

X and Y are each, independently of each other, H or OH, or together form a double bond, R is H or phosphorylcholine $-PO(=O)(-O^\bullet)(CH_2)_2N^+(CH_3)_3$ $R_1$ and $R_2$ are independently H or a lower alkyl group.

A lower alkyl group as $R_1$, and/or $R_2$ is preferably one with 1–3 carbon atoms, preferably methyl.

X is preferably H or forms a double bond with Y.

Especially contemplated for use in the invention are the sphingosine derivatives of the above formula selected from the group consisting of sphingosine, phytosphingosine, dihydrosphingosine and dimethylsphingosine.

According to the invention, the liposomal transfection vector includes also at least one helper lipid, which is not a sphingosine derivative. Such a lipid is typically selected from the group of neutral phospholipids, typically it is phosphatidylethanolamine, or a diacylglycerol. The helper lipid has fusogenic properties meaning that the lipid has the property of facilitating the fusion of lipid membranes, see e.g. Kinnunen, P. K. J., *Chem. Phys. Lipids*., 63 (1992) 251–258. However, within the context of the invention, any lipid which has fusogenic properties and which is neutral or which does not substantially alter the cationic nature of the formed liposome, can come into question.

According to a preferred embodiment of the invention the composition comprises a first helper lipid which is selected from fusogenic neutral phospholipids, especially from phosphatidylethanolamines, and a second helper lipid selected from diacyl glycerols.

A preferred phospholipid is phosphatidylethanolamine, especially dioleoylphosphatidylethanolamine (DOPE), or the corresponding dilauroyl, dimyristoyl and dipalmitoyl compounds. A preferred liposome composition of the invention contains from 10 to 90% by weight of helper lipid, such as phospholipid, in combination with 10 to 90% by weight of a sphingosine derivative. A more preferred composition is from 30 to 70% by weight of helper lipid and 70 to 30% by weight of a sphingosine derivative. As will be shown later, very good results have been obtained using DOPE and sphingosine in an amount of 1:1 (wt:wt), which corresponds to a molar ratio between the compounds of appr. 1:2.

According to a preferred embodiment of the invention, the cationic liposomal composition includes a glyceride, preferably a diacyl glycerol as a second helper lipid. According to the invention it has namely been shown that the transfection efficiency in terms of expression can be increased by incorporating an amount of diacyl glycerol in the composition. For the purpose of the invention, especially a diacyl glycerol selected from dioleoylglycerol and dioctanoylglycerol, are contemplated. Diacyl glycerol, when included as a second helper lipid, is included in an amount of up to 25 mole % calculated from the lipid composition of the liposome. Optimal results have been obtained using appr. 5 to 10 mole % of such diacyl glycerols (calculated of total lipids).

The preparation of the liposomes to be used according to the invention is well known to a person skilled in the art, see for example Kinnunen P. K. J., et al., *Chem. Phys. Lipids* 66 (1993) 75–85, describing the preparation of multilamellar liposomes. Briefly, sphingosine and any further lipids to be used are mixed in a suitable solvent, e.g. in chloroform, and evaporated to dryness under a stream of nitrogen. To prepare the liposomes, the thus dried lipid mixture is hydrated in a buffer, including short periodical vortexing, and sonicated at the end of the hydration period, to form multilamellar liposomes.

Nucleic acid includes in this context DNA and RNA, and oligonucleotides of DNA and RNA.

To prepare the nucleic acid-lipid complex, the nucleic acid and the lipids are each diluted in an appropriate medium, for example in serum-free DMEM (Dulbecco's Modified Eagle's Medium), mixed and preincubated for a suitable period of time. The amount of nucleic acid to lipid can vary, but a weight ratio between nucleic acid and lipid in the range of 0.25:15 to 4:5 has been found to be satisfactory. Due to charge interactions, the nucleic acid forms a strong complex with the cationic liposome surface after simple mixing of the components. Good transfection results have been obtained in tests using 1 or 2 μg respectively of DNA to 10 μg of total lipid. The concentration of nucleic acid in the transfection medium is suitably adjusted to 1 to 2 μg/ml.

The term "cell" means in this context an animal cell or a plant cell. Unicellular organisms as well as multicellular organisms or systems such as cell cultures are contemplated in the invention.

Methods of transfection are well known in the art and such known methods can be used with the present liposome compositions as well. The invention thus concerns an improved method of transfection, the improvement comprising using, as the transfection vector, a liposome comprising a nucleic acid and a sphingosine derivative, and preferably a helper phospholipid.

The method according to the invention is useful when it is desirable to deliver a nucleic acid to a cell, particularly in situ. In situ is intended to include the terms in vivo and in vitro.

In the method according to the invention, liposomes made from non-toxic lipids are used, wherefore they are applicable for in vivo use in different gene therapies. The liposomes may be administered topically or injected, e.g. in the blood stream, directly into a tissue, into the peritoneum, or converted to an aerosol, or applied topically on or implanted in a blood vessel wall. One example is the treatment of tumours in which liposomes containing a toxic gene (e.g. Herpex simplex thymidine kinase) can be injected directly into the tumour, or into a body cavity (e.g. pleural cavity, liquor space). The gene is expressed in the tumour tissue and destroys its cells. Another application of the invention is in male contraception, whereby liposomes are injected retrogradely into the semen duct, and from there to the epididymis. The liposomes can contain DNA that encodes for antisense-RNA, which inhibits the function of the genes responsible for the maturing of the spernatozoa of the epididymis.

The liposome containing preparations to be used in the method of the invention are applied in therapeutically acceptable amounts to produce therapeutically effective levels in the target without producing clinically unacceptable adverse effects. Such preparations for use may routinely contain per se known compatible carriers, and other additives, such as buffering agents and preservatives, and optionally other therapeutical agents. Aqueous liposomal preparations may be formulated according to known methods using suitable additivies, such as dispersing or wetting agents and suspending agents. A sterile injectable preparation may be a sterile injectable solution or suspension in a non-toxic parenterally acceptable diluent or solvent, such as water and isotonic sodium chloride solution. In addition, sterile oils are conventionally employed as a solvent or suspending medium.

The particular mode of administration selected will depend, of course, upon the particular drug selected, the severity of the condition being treated and the dosage required for therapeutic efficacy. Such modes of administration include oral, rectal, topical, nasal, interdermal, or parenteral routes, the term parenteral including subcutaneous, intravenous, intramuscular, and infusion.

The invention will be described in more detail in the following examples, referring to enclosed drawing, wherein

EXAMPLES

Preparation of a Transfection Liposome

Figure 1:
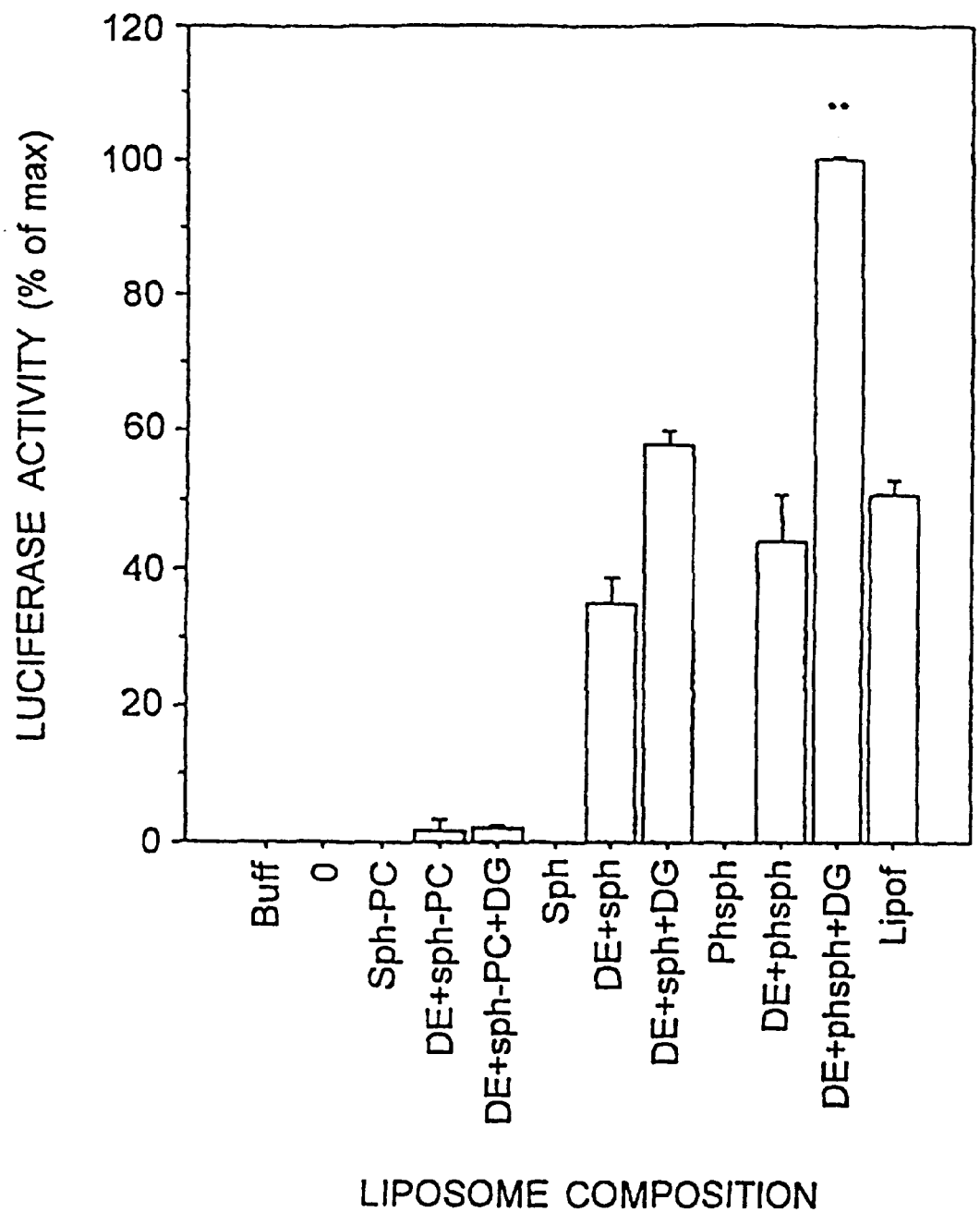
FIG. 1 shows the effect of different liposomal combinations on the transfection efficiency of pCMV-luci in KK-1 cells. KK-1 cells were transfected with 10 µg lipid and 1 µg CMV-luci plasmid. After harvest, the luciferase activity of the cell lysates were measured. Buff=cells not transfected; 0=cells transfected with 1 µg DNA only, with no liposomes; sph-PC=sphingosylphosphorylcholine; sph=sphingosine; phsph=phytosphingosine; DE=DOPE; DG=DOG; DOPE and sphingosine were mixed 1:1 (wt:wt) and 10 mole % of DOG was added were indicated.

Liposomes were prepared using lipid stocks of DOPE and of appropriate sphingosine derivative selected from sphingosine, phytosphingosine and phosphorylcholine-sphingosine. The lipids chosen were dissolved in chloroform at a ratio of 1:1 (by weight). To the solution obtained either dioleoylglycerol (DOG) or dioctanoylglycerol (DOcG) were added in indicated amounts, up to 30 mole %. The solvent was evaporated under a stream of nitrogen and the drying was continued in a lyophilizator for at least 2 hours or overnight. Thereafter the dry lipid mixture was hydrated in a buffer containing 20 mM Hepes, 150 mM NaCl, 0.1 EDTA, pH 7.4, for 30 minutes at 40° C. in a water bath, and vortexed briefly every 5 minutes. At the end of hydration the liposomes obtained were sonicated for appr. 5 minutes. The total lipid concentration of the liposomes was usually 100 µg/ml buffer. The liposomes prepared were kept in a refrigerator, in closed test tubes.

Lipofectin® "LIPOFECTIN" was used as the reference liposome vector according to the instructions of the manufacturer.

Preparation of DNA-lipid complexes

The pCMV-luciferase construct used in the experiments was designed to carry the promoter area of the cytomegalo virus in front of the firefly luciferase coding sequence in an expression vector PUHC13-1 (Gossen M., and Bujard H., Proc. Natl. Acad. Sci. 89 (1992), 5547–5551). The DNA preparation was purified twice with CsCl gradient centrifugation and dissolved in sterile water for the transfections. The identity of the CMV-Luciferase construct was verified using the specific restriction endonuclease digestion.

DNA and the lipid were each diluted to 100 µl of serum free DMEM (DMEM-SF) and then mixed 1 µg of lipid and 2 µg, respectively, of DNA and 10 µg of total lipid were pre-incubated for 15 minutes. Thereafter the total volume of the mixture was adjusted to 1 ml with DMEM-SF. The DNA-lipid complexes formed rapidly after mixing and had a stable transfectability at least for one hour at the concentration used.

Transfection

As cell cultures the cell line KK-1 and HeLa cells were used. The KK-1 cells were derived from transgenic murine ovarian tumour cells immortalized by expression of the simian virus 40 large and small tumour (T) antigens under the control of inhibin-α subunit promoter (Kananen K., et al. Mol. Endocrinol. 9 (1995) 616–627). The HeLa cells are derived from human uterine cervix carcinoma (see e.g. Gossen, M. et al., Proc. Nati. Acad. Sci. USA 89 (1992) 5547–5551). The cells were grown on plastic tissue culture plates in Dulbecco's modified Eagle's medium with 10% fetal bovine serum (DMEM-10) in an incubator in an atmosphere of 5% $CO_2$ in air at 37° C.

At least 80% confluent six-well cell culture plates were washed with DMEM-SF and the DNA-lipid complexes were laid over the cells. For each well 1 µg DNA/10 µg liposome was used for KK-1 cells and 2 µg/10 µg liposomes for HeLa cells. For each test, 2–3 parallel wells were used. After a 10 hour incubation period at 37° C., the DNA-lipid mixture was replaced by 2 ml of DMEM-10. Three days after beginning of transfection, the cells were harvested by scraping off the culture plates. The cell extracts were prepared and a luminometric assay for luciferase activity was performed by measuring the activity of the protein (the ATP Luciferaso enzyme) produced by the cells, by measuring the degradation of ATP by the luciferase enzyme (see e.g. Gould S., et al., Anal. Biochem. 7 (1988), 5–13; Nguyen V., Anal. Biochem. 171 (1988) 404–408. In brief, 50 µl of the total of 100 µl of the cell extracts were mixed with 360 µl of assay buffer by short vortexing in a disposable cuvette. The cuvettes were thereafter placed in a Bio-Orbit Luminometer 1252 (Bio- Orbit Ltd., Turku, Finland) and the luminesence was measured after adding 200 μl of luciferin solution. When the luciferase activity of a sample was exceeding the measuring range, a smaller amount (10 or 20 μl) of the cell extract was used at re-measurement.

In order to measure PKC stimulation, phorbol myristic acid (PMA) (1% of moles of lipids) was added to the liposome solutions. Transfection and expression analysis were performed as described above.

Results

Figure 2:
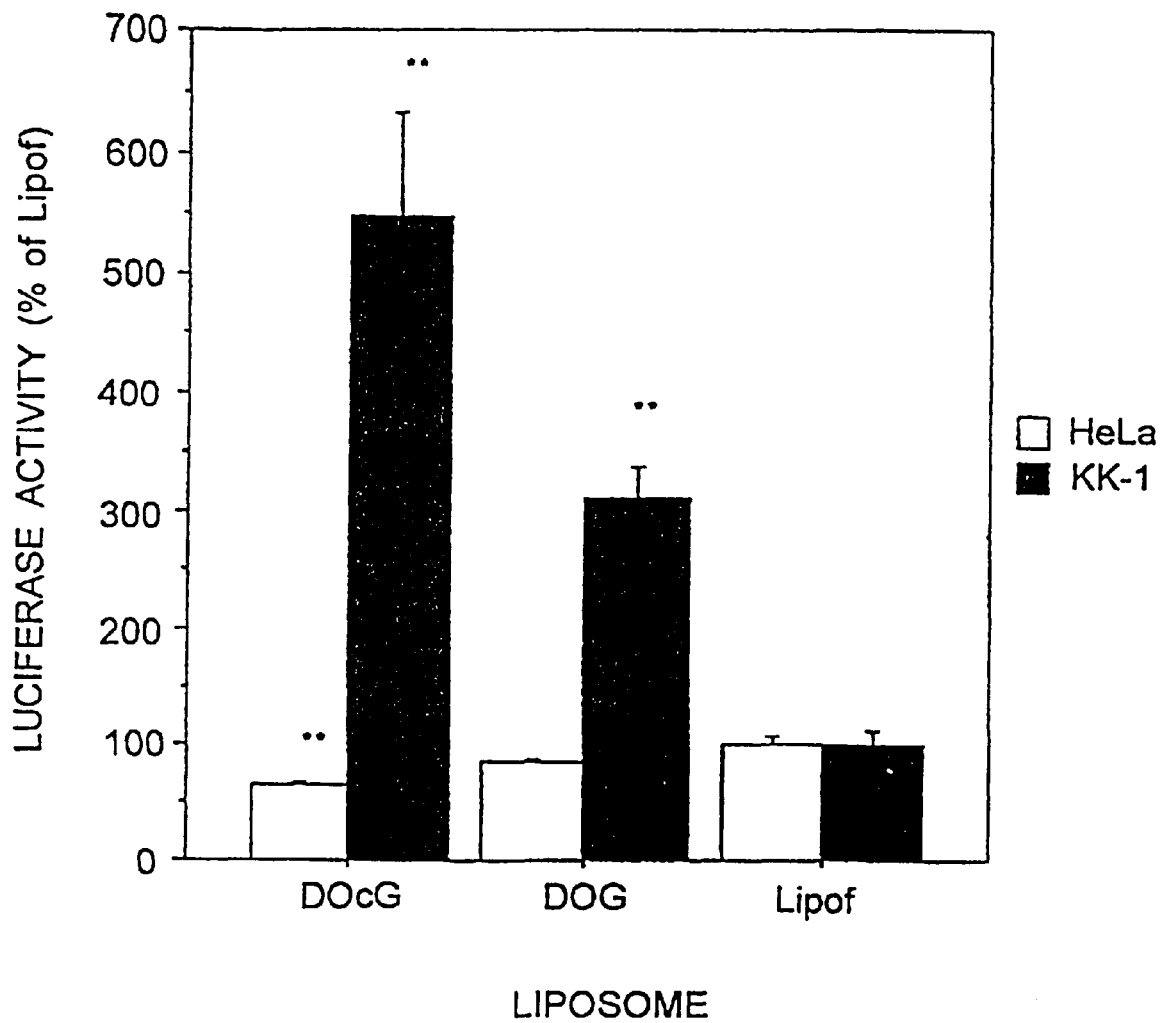
FIG. 2 shows the transfection efficiency of DOPE-phytosphingosine liposomes added with 5 mole % of either dioctanoylglycerol (DOcG) or dioleoylglycerol (DOG) and tested on HeLa and KK-1 cells. 10 µg of lipid and 2 µg (HeLa cells) or 1 µpq (KK-1 cells) of DNA was used in the transfaction. The expression was compared to that in the cells transfected with Lipofectin® "LIPOFECTIN".

As is evident from the FIG. 1, the phytosphingosine and sphingosine containing liposomes showed major transfection efficiency in KK-1 cells comparable to or exceeding that of Lipotectin® "LIPOFECTIN". The transfection efficiency is poor in compositions not containing DOPE. The transfection efficiency in HeLa cells was somewhat poorer than that in KK-1 cells, see FIG. 2.

After incubation of KK-1 cells with liposomes for 16 h or longer, the cells transfected with Lipofectin® "LIPOFECTIN" had almost all died, whereas the sphingosine liposomes showed no marked cell death. The HeLa cells tolerated better Lipofectin® "LIPOFECTIN" showing less damage after incubation periods over 10 hours.

Figure 3A:
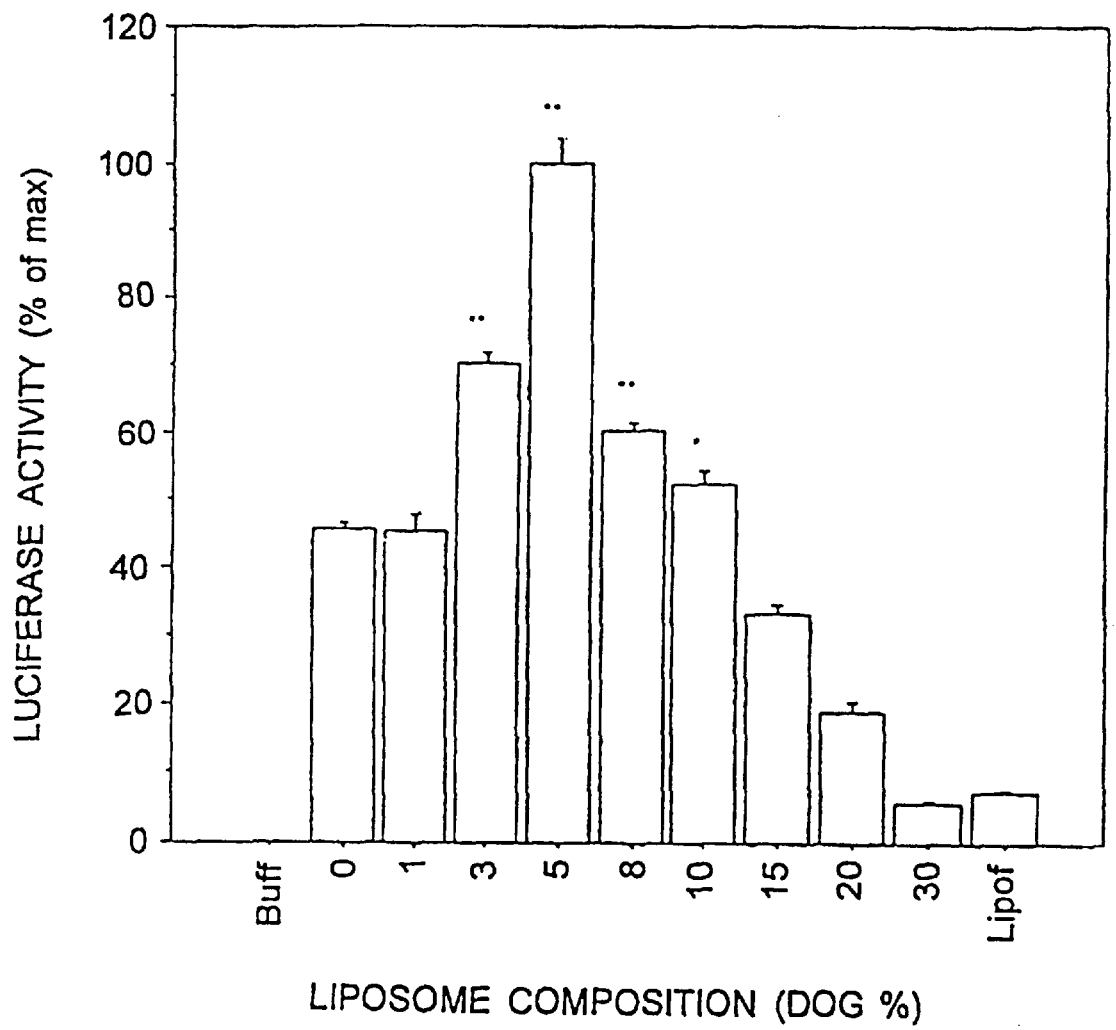
FIG. 3a shows the effect of adding different molar percentages of DOG into DOPE-phytosphingosine liposomes. 10 µg of total lipid and 1 µg of DNA was used to transfect KK-1 cells.
Figure 3B:
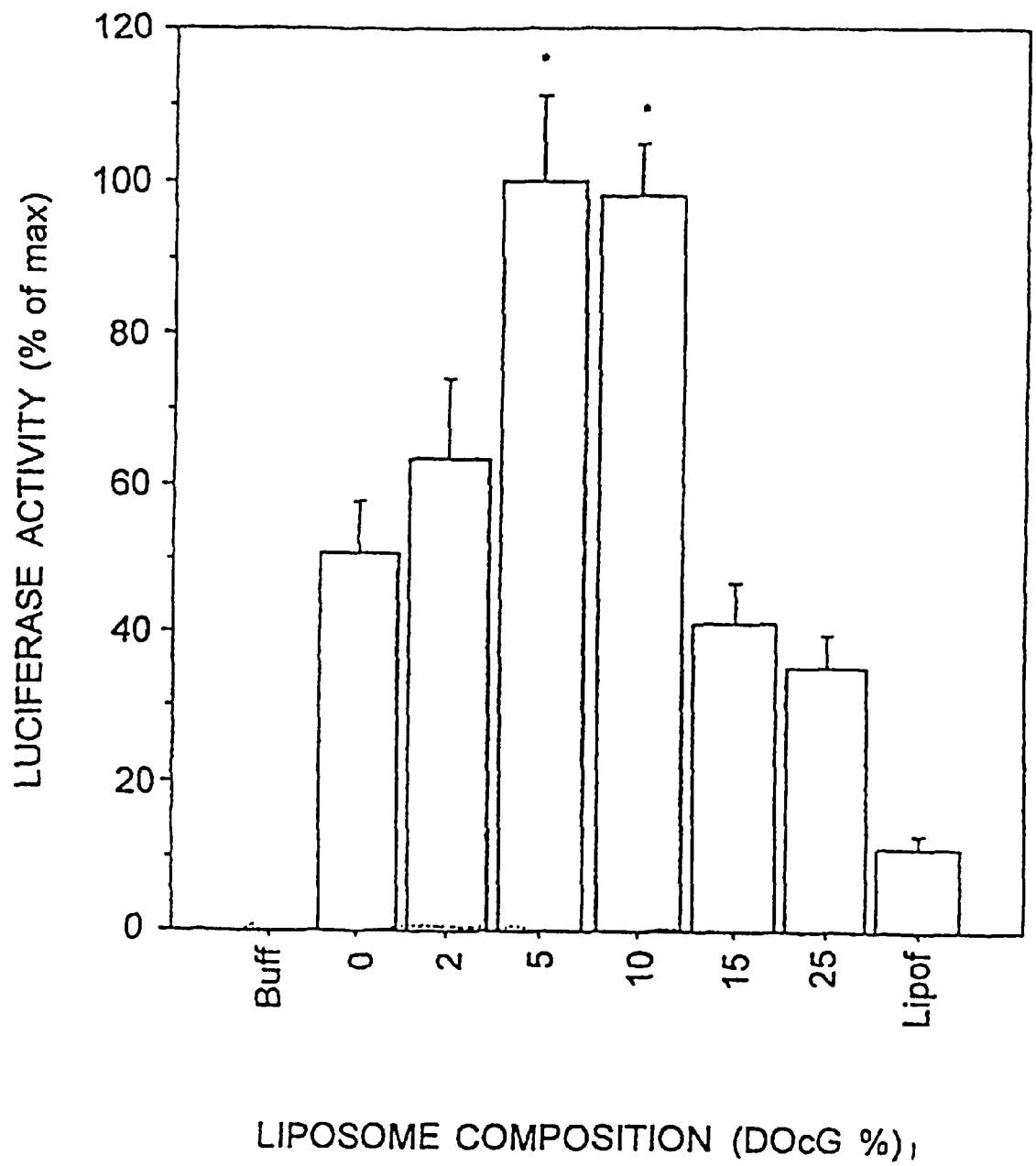
FIG. 3b shows the effect of combining different molar percentages of DOcG into DOPE-phytosphingosine liposomes, 10 µg of total lipid and 1 µg of DNA was used to transfect KK-1 cells.

Adding diacylglycerol to the sphingosine lipid composition affected the transient luciferase expression in a biphasical dose dependant manner (FIG. 3). From the results it is evident that dioleoylglycerol doubled the transfection at the optimal 5% molar concentration, and that dioctanoylglycerol was most efficient at 5 to 10% molar concentrations. Concentrations higher than appr. 25 molar % gave no improvement but rather caused lower expression. In wells stimulated by PMA, the expression was only a fourth of those not stimulated.

Figure 4:
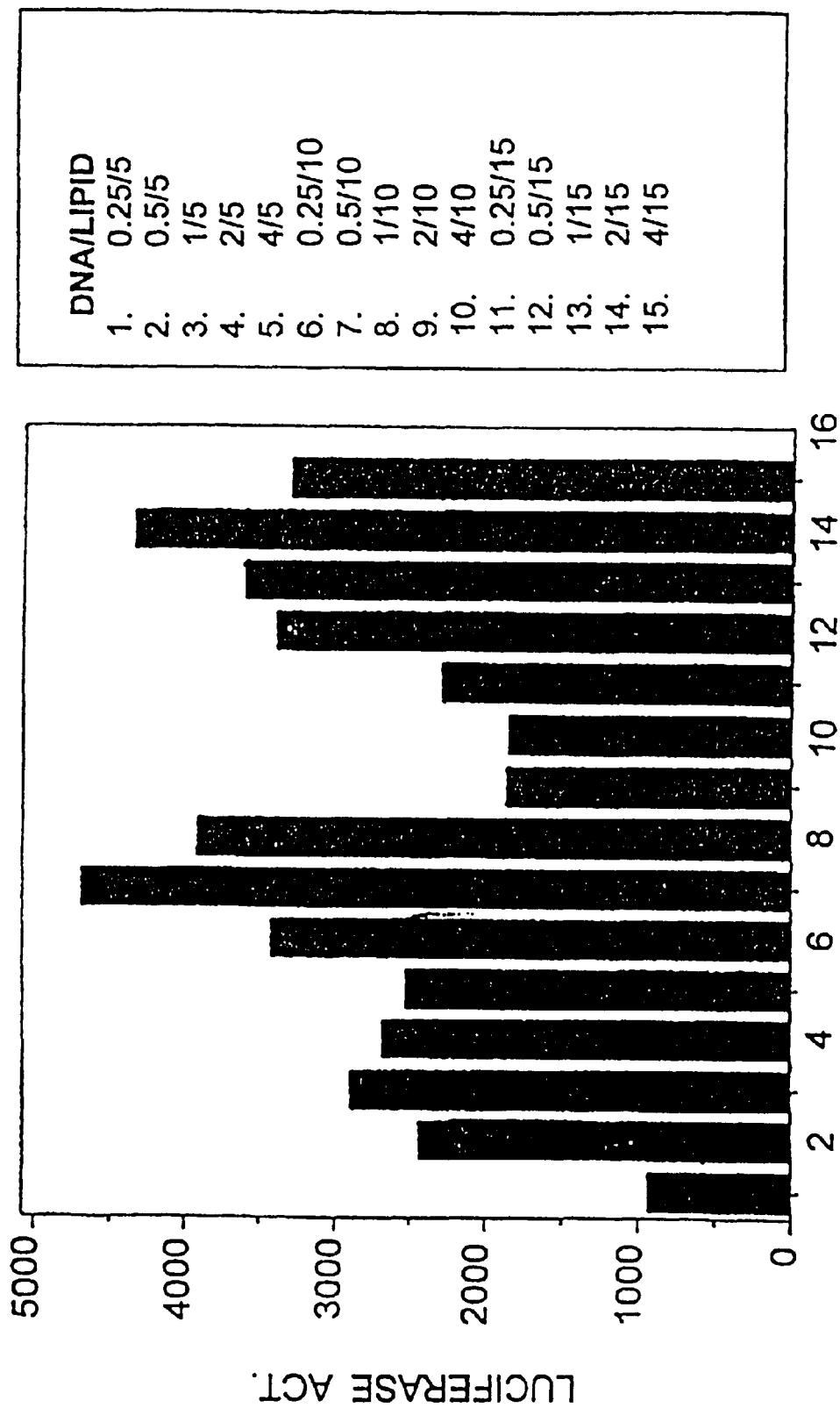
FIG. 4 shows the transfection efficiency using various DNA/total lipid ratios on KK-1 cells. The liposome composition was DOPE:phytosphingosine in a ratio of 1:1 (wt:vvt) and 5 mole % of DOG.
Figure 5:
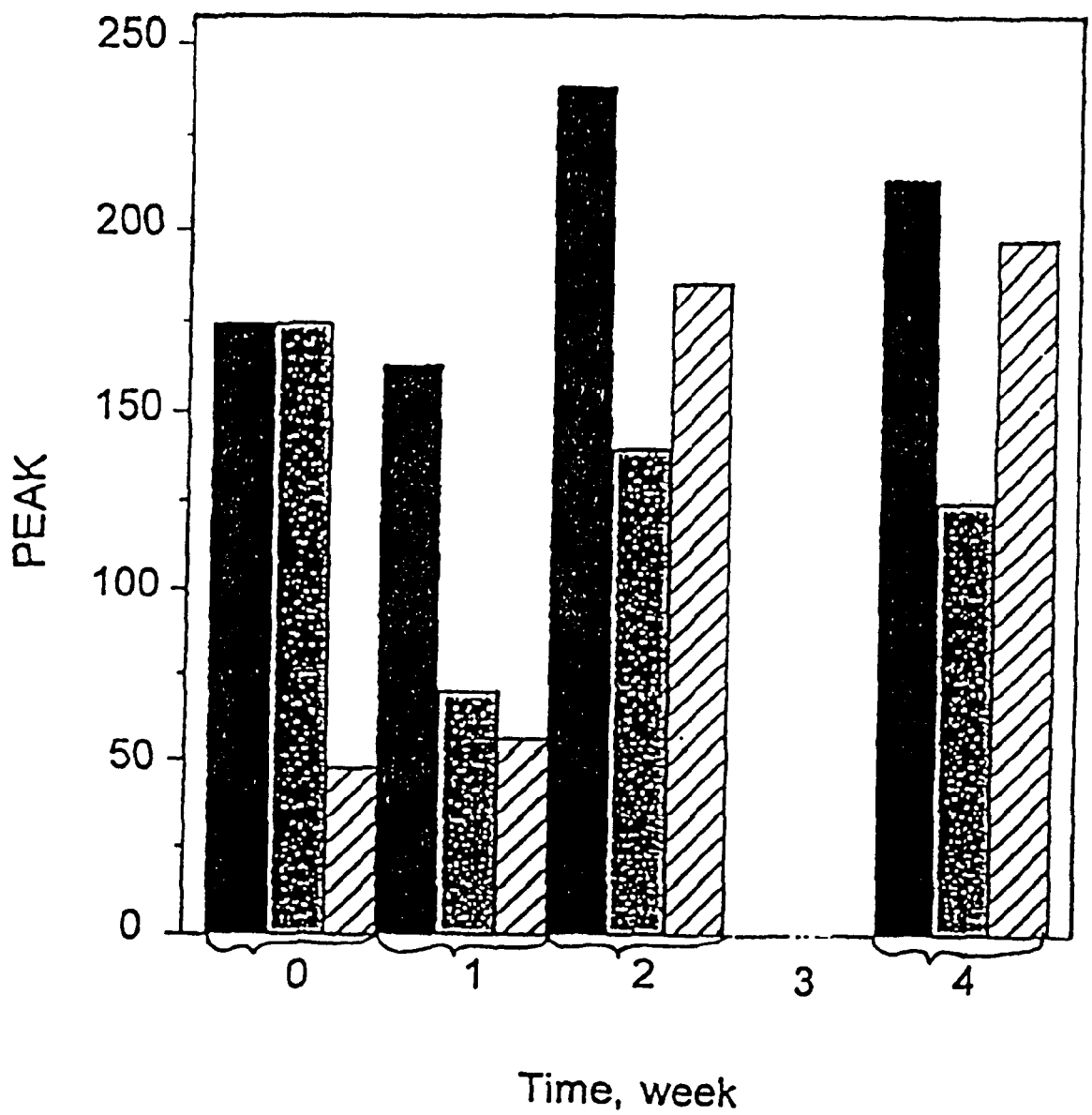
FIG. 5 shows the results of storage tests of liposomes carried out on KK-1 cells. The dark column represents storage for a composition according to the invention (composition as in FIG. 4 except that DOcG was used instead of DOG) stored at +4° C. and the grey column that of the same composition stored at −20° C. The striped column represents storage results for Lipofectin® "LIPOFECTIN" stored at +4° C. according to the instructions of the manufacturer.

The results shown in FIG. 4 show that the DNA/lipid ratio is not very critical and that ranges from 0.25 μg/15 μg to 4 μg/5 μg gave satisfactory results. The storage test results of FIG. 5 indicate that the compositions for use according to the invention have at least comparable storage characteristics as compared to Lipofectin® "LIPOFECTIN".

The results show that the toxicity of the sphingosine derivative containing liposomes on cells, such as KK-1 cells, apparently is lower than that of the widely used transfection liposomal preparation Lipofectin® "LIPOFECTIN". It is contemplated that the non-biodegradabale DOTMA included in Lipofectin® "LIPOFECTIN" may account for the difference. Thus especially sensitive cell lines could more easily be handled with less toxic vectors. Some special cellular functions may also be disturbed in dying cells, e.g. promoter function experiments might be aberrated due to toxic effects. The PKC activators can increase the transfection efficiency by the calcium phosphate method (Reston J., et al., *Biochem. Biophys. Acta* 1088 (1991), 270–276). According to the invention, however. adding PMA to the liposome solution lowered the expression of the luciferase gene. The PKC activity thus seems to affect the sphingolipid liposome mediated transfection in opposite fashion, as compared with calcium phosphate transfection.

The availability and low cost of the components used according to the invention is a well acknowledged benefit in practice. The liposomes are easily prepared and the time consumption is modest. Hence the sphingosine derivative based liposomes are an efficient, low toxicity alternative for DNA transfection to cells in vitro. They may be of use also in transfection of other materials and in in vivo transfection.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting. The invention is limited only as defined in the following claims and the equivalents thereto.

What is claimed is:

1. An improvement in a method for transfecting a cell with a nucleic acid, the improvement comprising contacting the cell in vitro with a liposomal transfection composition comprising the nucleic acid sphingosine or a derivative of sphingosine of the formula:

wherein X and Y are each, independently of each other H or OH, or together form a double bond, wherein R1 and R2 are independently H or a lower alkyl group, and a helper lipid wherein the nucleic acid is delivered to the cell.

2. The improvement according to claim 1, wherein the helper lipid is a neutral phospholipid.

3. The improvement according to claim 2, wherein the phospholipid is a phosphatidylethanolamine.

4. The improvement according to claim 2, wherein the composition comprises a diacyl glycerol as an additional helper lipid.

5. The improvement according to claim 1, wherein the sphingosine derivative is selected from the group consisting of phytosphingosine, dihydrosphingosine and dimethylsphingosine.

6. The improvement according to claim 2, wherein the phospholipid is dioleoylphosphatidylethanolamine (DOPE).

7. The improvement according to claim 2, wherein the phospholipid is a phosphatidylethanolamine and the composition comprises an additional helper lipid selected from the group consisting of dioleoylglycerol and dioctanoylglycerol.

8. The improvement according to claim 2, wherein the composition further comprises a compound selected from the group consisting of cholesterol and sterol.

9. The improvement according to claim 1, wherein the composition comprises dioleoylphosphatidylethanolamine and a diacylglycerol selected from the group consisting of dioleoylglycerol and dioctanoylglycerol.

10. The improvement according to claim 1 or 2, wherein the composition contains sphingosine or the derivative of sphingosine in an amount of 10 to 90% by weight and a helper lipid in an amount from 10 to 90% by weight, calculated from the combined weight of sphingosine or the derivative of sphingosine, and the helper lipid.

11. The improvement according to claim 1 or 2, wherein the composition contains sphingosine or the derivative of sphingosine in an amount of 30 to 70% by weight and a helper lipid in an amount from 30 to 70% by weight, calculated from the combined weight of sphingosine or the derivative of sphingosine, and the helper lipid.

12. The improvement according to claim 1 or 2, wherein the ratio between sphingosine or the derivative of sphingosine and the helper lipid is approximately 1:1 (wt/wt).

13. The improvement according to claim 2, wherein the composition contains sphingosine or the derivative of sphingosine in an amount of 30 to 70% by weight and phospholipid in an amount from 30 to 70% by weight, calculated from the combined weight of sphingosine or the derivative of sphingosine, and the phospholipid, and a diacyl glycerol as an additional helper lipid in an amount of up to 25 mole -% calculated on the total amount of lipids.

14. The improvement according to claim 2, wherein the composition contains sphingosine or the derivative of sphingosine in an amount of 30 to 70% by weight and phospholipid in an amount from 30 to 70% by weight, calculated from the combined weight of sphingosine or the derivative of sphingosine, and the phospholipid, and a diacyl glycerol as an additional helper lipid in an amount of 5 to 10 mole -% of the diacyl glycerol, calculated on the total amount of lipids.

15. The improvement according to claim 1, wherein the ratio between nucleic acid and total lipids is 0.25:15 to 4:5 (wt/wt).

16. The improvement according to claim 1, wherein the lipid composition comprises 30 to 70% by weight of a compound selected from the group consisting of sphingosine and phytosphingosine, and 30 to 70% by weight of dioleoylphosphatidylethanolamine, the said % by weight being calculated on the combined weight of sphingosine and phosphatidylethanolamine compounds, and in addition 5 to 15 mole %, calculated from the amount of total lipids, of a compound selected from the group consisting of dioleoylglycerol and dioctanoylglycerol.

17. A method for delivery of a nucleic acid to a cell of a subject comprising administering to the surface of the cell of the subject a liposomal transfection composition comprising:

the nucleic acid sphingosine or a derivative of sphingosine of the formula:
wherein X and Y are each, independently of each other H or OH, or together form a double bond, wherein R1 and R2 are independently H or a lower alkyl group, and a helper lipid, wherein the nucleic acid is delivered to the cell.

18. The method according to claim 17 wherein the helper lipid is a neutral phospholipid.

19. The method according to claim 18 wherein the phospholipid is a phosphatidylethanolamine.

20. The method according to claim 18 wherein the composition comprises a diacyl glycerol as an additional helper lipid.

21. The method according to claim 17 wherein the sphingosine derivative is selected from the group consisting of sphingosine, phytosphingosine, dihydrosphingosine and dimethylsphingosine.

22. The method according to claim 18 wherein the phospholipid is dioleoylphosphatidylethanolamine.

23. The method according to claim 18 wherein the phospholipid is a phosphatidylethanolamine and the composition comprises an additional helper lipid selected from the group consisting of dioleoglycerol and dioctanoylglycerol.

24. The method according to claim 18 wherein the composition further comprises a compound selected from the group consisting of cholesterol and sterol.

25. The method according to claim 17 wherein the composition comprises dioleoylphosphatidylethanolamine and a diacylglycerol selected from the group consisting of dioleoylglycerol and dioctanoylglycerol.

26. The method according to claim 17, wherein the composition contains sphingosine or the derivative of sphingosine in an amount of 10 to 90% by weight and a helper lipid in an amount from 10 to 90% by weight, calculated from the combined weight of sphingosine or the derivative of sphingosine, and the helper lipid.

27. The method according to claim 17, wherein the composition contains sphingosine or the derivative of sphingosine in an amount of 30 to 70% by weight and a helper lipid in an amount from 30 to 70% by weight, calculated from the combined weight of sphingosine or the derivative of sphingosine, and the helper lipid.

28. The method according to claim 17, wherein the ratio between sphingosine or the derivative of sphingosine and the helper lipid is approximately 1:1 (wt/wt).

29. The method of claim 18, wherein the composition contains sphingosine or the derivative of sphingosine in an amount of 30 to 70% by weight and phospholipid in an amount from 30 to 70% by weight, calculated from the combined weight of sphingosine or the derivative of sphingosine, and of the phospholipid, and a diacyl glycerol as an additional helper lipid in an amount of up to 25 mole -% calculated on the total amount of lipids.

30. The method according to claim 18, wherein the composition contains sphingosine or the derivative of sphingosine in an amount of 30 to 70% by weight, and phospholipid in an amount from 30 to 70% by weight, calculated from the combined weight of sphingosine or the derivative of sphingosine, and of the phospholipid, and a diacyl glycerol as an additional helper lipid in an amount of 5 to 10 mole -% of the diacylglycerol, calculated on the total amount of lipids.

31. The method according to claim 17 wherein the ratio between nucleic acid and total lipids is between 0.25:15 and 4:5 (wt/wt).

32. The method according to claim 17 wherein the lipid composition comprises: 30 to 70% by weight of a compound selected from the group consisting of sphingosine and phytosphingosine, 30 to 70% by weight of dioleoylphosphatidylethanolamine, the said % by weight being calculated on the combined weight of sphingosine and phosphatidylethanolamine compounds, and in addition 5 to 15 mole % calculated from the amount of total lipids, of a compound selected from the group consisting of dioleoylglycerol and dioctanoylglycerol.

* * * * *